US00PP24723P3

(12) United States Plant Patent
Warren et al.

(10) Patent No.: US PP24,723 P3
(45) Date of Patent: Jul. 29, 2014

(54) CALLA LILY PLANT NAMED 'AMARILLO BLZ'

(50) Latin Name: ***Zantedeschia* spp.**
Varietal Denomination: Amarillo BLZ

(76) Inventors: Andrew G. F. Warren, Tauranga (NZ); Jacobus P. Spaans, Tauranga (NZ)

( * ) Notice: Subject to any disclaimer, the term of this patent is extended or adjusted under 35 U.S.C. 154(b) by 176 days.

(21) Appl. No.: 13/507,568

(22) Filed: Jul. 11, 2012

(65) Prior Publication Data

US 2014/0020145 P1 Jan. 16, 2014

(51) Int. Cl.
*A01H 5/00* (2006.01)

(52) U.S. Cl.
USPC ..... Plt./490

(58) Field of Classification Search
CPC ..... A01H 5/02
USPC ..... Plt./490
See application file for complete search history.

*Primary Examiner* — June Hwu

(57) ABSTRACT

A calla lily plant particularly distinguished by yellow spathes, medium density maculation of the leaves that is visible from both sides of the leaf and produces 2 to 3 inflorescences per 3-cm tuber, is described.

3 Drawing Sheets

Genus and species: *Zantedeschia* spp.
Variety denomination: 'Amarillo BLZ'.

BACKGROUND OF THE NEW PLANT

The present invention comprises a new and distinct cultivar of calla lily, botanically known as *Zantedeschia* spp., and hereinafter referred to by the cultivar name 'Amarillo BLZ'. The new cultivar was asexually reproduced by tissue culture resulting from the cross of the female parent an unnamed, unpatented *Zantedeschia* variety having yellow spathes and the male parent Florex Gold, an unpatented *Zantedeschia* variety having yellow spathes. 'Amarillo BLZ' is a product of a planned breeding program intended to create new calla lily plants with yellow spathes.

The new cultivar was created in Tauranga, New Zealand and has been asexually reproduced repeatedly by tissue culture in Bangalore, India over a two year period. The present invention has been found to retain its distinctive characteristics through successive propagations.

Plant Breeder's Rights for this cultivar were applied for in New Zealand on Apr. 28, 2011. 'Amarillo BLZ' has not been made publicly available anywhere in the world more than one year prior to the filing date of this application.

SUMMARY OF THE INVENTION

The following are the most outstanding and distinguishing characteristics of this new cultivar when grown under normal horticultural practices in Tauranga, New Zealand.

1. Yellow spathes;
2. Medium density maculation of the leaves that is visible from both sides; and
3. Produces 2 to 3 inflorescences per 3-cm tuber.

DESCRIPTION OF THE PHOTOGRAPHS

This new calla lily plant is illustrated by the accompanying photographs which show the plant habit, mature inflorescence and foliage of the plant. The colors shown are as true as can be reasonably obtained by conventional photographic procedures. The photographs are of a plant approximately 9 weeks old, after planting in optimum conditions.

Figure 1:
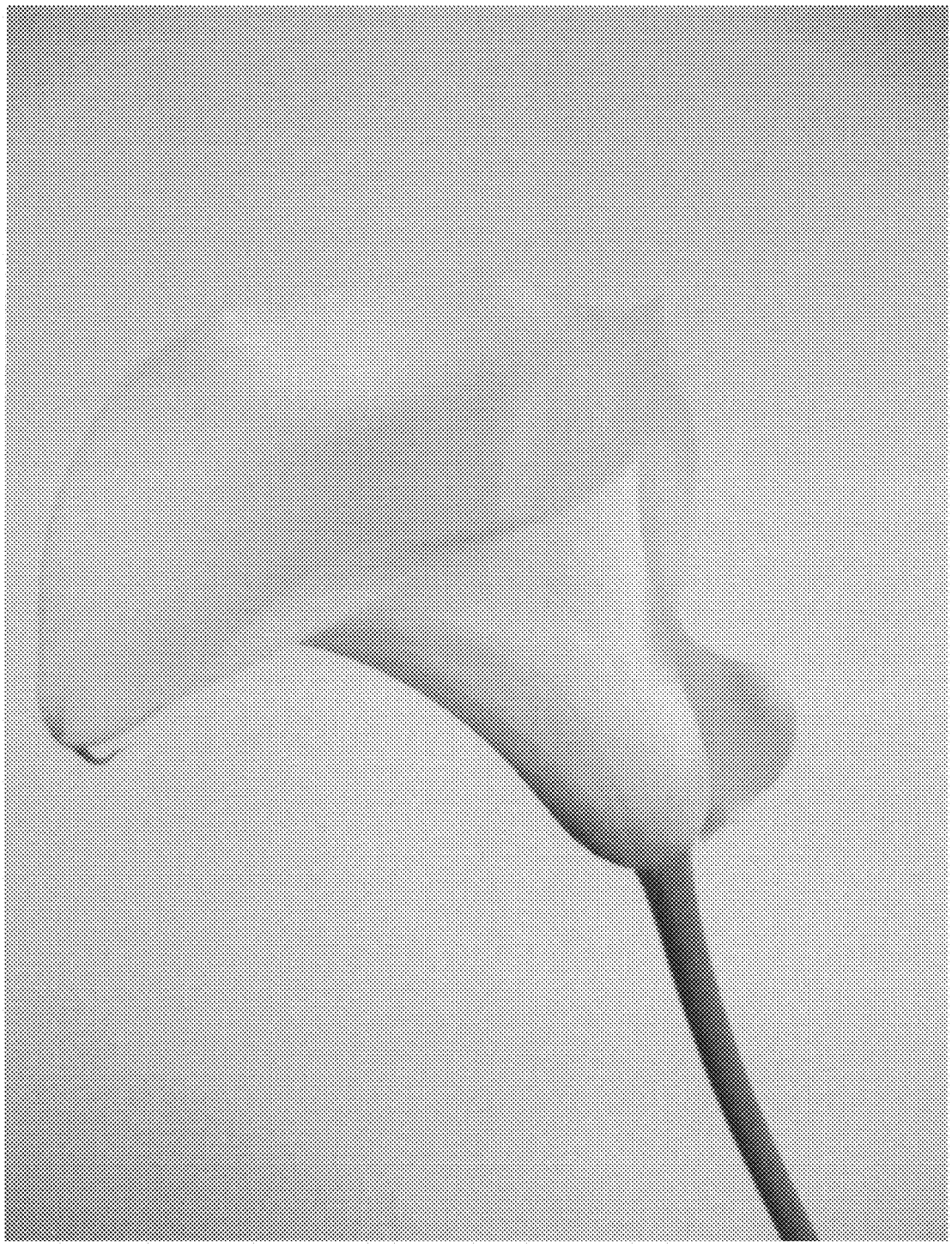
Figure 2:
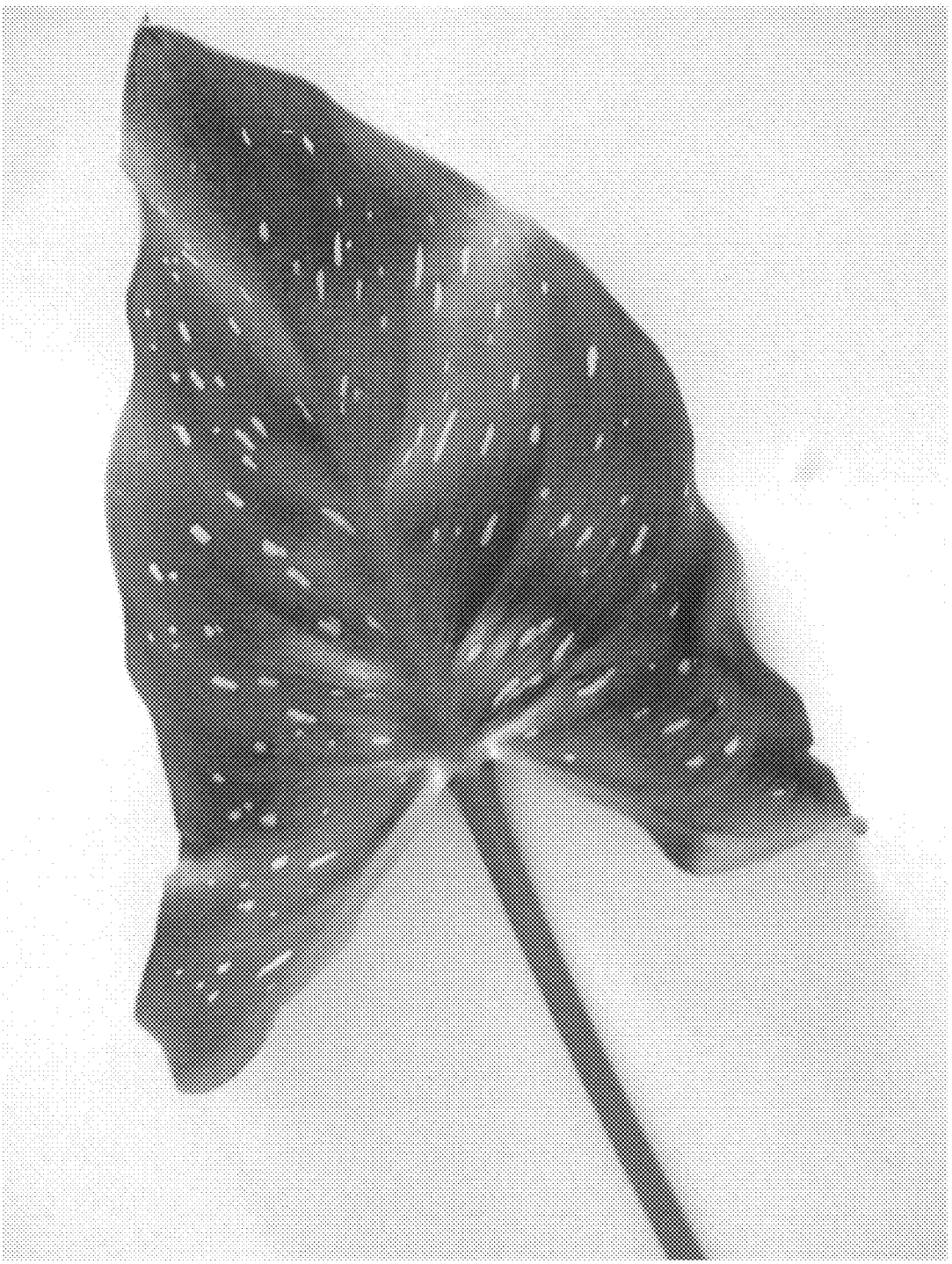
Figure 3:
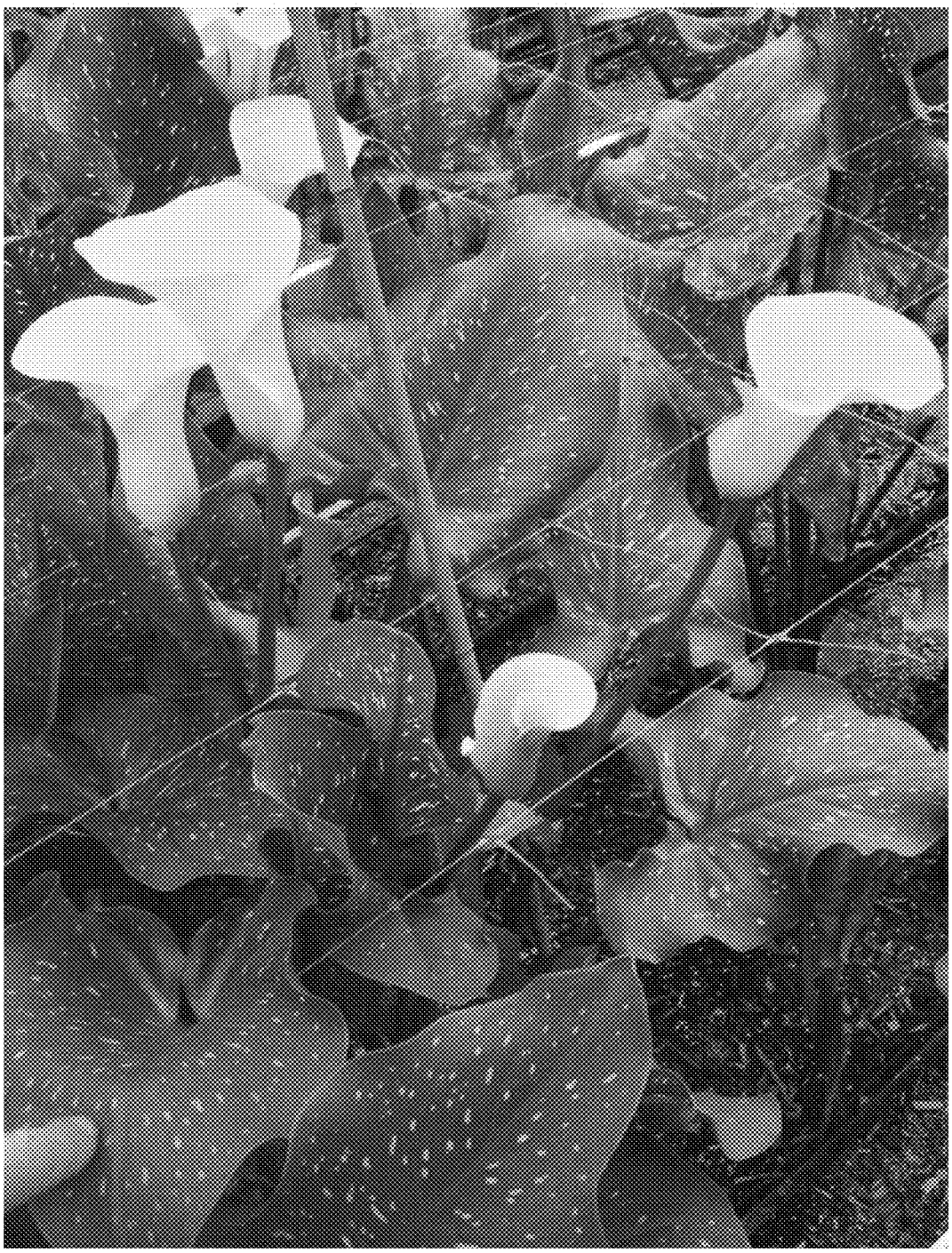

FIG. 1 shows a close-up of the mature inflorescence.
FIG. 2 shows a close-up of the leaf and maculation.
FIG. 3 shows the mature inflorescence and foliage.

DESCRIPTION OF THE NEW CULTIVAR

The following detailed description sets forth the distinctive characteristics of 'Amarillo BLZ'. The data that define these characteristics were collected from asexual reproductions carried out in New Zealand. The plant history was taken on plants of two-year-old tubers based on a 3-cm diameter tuber under New Zealand summer conditions. Color references are primarily to The 1995 edition of The Colour Chart of The Royal Horticultural Society of London (R.H.S.)

DETAILED BOTANICAL DESCRIPTION

Classification:
- *Family*.—Araceae.
- *Botanical name*.—*Zantedeschia* spp.
- *Common name*.—Calla lily.

Parentage:
- *Female parent*.—An unnamed, unpatented *Zantedeschia* variety having yellow spathes.
- *Male parent*.—Florex Gold, an unpatented *Zantedeschia* variety having yellow spathes.

Plant:
- *Form*.—Erect.
- *Height of the leaf canopy above the soil*.—40 cm to 50 cm.
- *Height of top of inflorescence above the soil*.—45 cm to 60 cm.
- *Diameter*.—25 cm to 40 cm.
- *Number of inflorescences per tuber size*.—Tuber diameter 3 cm: 2 to 3. Tuber diameter 4 cm: 3 to 5. Tuber diameter 5 cm: 5+.
- *Flowering habit*.—Continuous for the 3 to 4 week flowering period.
- *Blooming season*.—Late spring and summer.

*Time to produce a finished flowering plant.*—6 to 10 weeks depending on the climate and environment.

*Lastingness of the inflorescence on the plant.*—2 to 3 weeks.

Tuber shoots:

*Character.*—Strong.

*Color.*—Upper: RHS 137A. Lower: RHS 137C. Base: RHS 155D.

*Average number.*—4 to 6.

Leaves:

*Size.*—Length: 18 cm to 23 cm. Width: 12 cm to 15 cm.

*Shape.*—Saggitate (arrow-shaped).

*Apex.*—Obtuse.

*Margin.*—Wavy.

*Margin color.*—Green.

*Venation patter.*—Pinnate.

*Surface texture.*—Leathery.

*Color.*—Upper surface: RHS 137A. Lower surface: RHS 137C.

*Maculation* (*leaf spots*).—General: Maculation is only on the upper surface of the leaf but is visible from the lower surface. Density: Medium density. Color: RHS 155C (white).

*Petiole.*—Average number per tuber: 4 to 6. Length: 18 cm to 25 cm. Diameter: 0.8 cm to 1.2 cm. Texture: Smooth. Character: Strong. Color: Base: RHS 59C. Upper portion: RHS 137B. Sheath: Length: 2 cm to 5 cm. Diameter: 0.6 cm to 0.8 cm. Color: RHS 59C (strongly mottled).

Roots:

*Color.*—RHS 155D (white).

*Branching.*—Not branched, attached to the top of the tuber at the apices.

Inflorescence:

*Spathe* (*flower body*).—Size: Length: 6.5 cm to 8.5 cm. Width: 6 cm to 7 cm. Height: 7 cm to 10 cm. Color: Upper portion: RHS 12A. Lower portion: RHS 12B. Outer surface of the base: some green coloration RHS 137D. Fading: does not fade. Vein color: RHS 12A. Throat spot: Medium-large, RHS 187A. Fragrance: None. Shape: Round. Texture: Smooth. Apex: Acute. Base: Attenuate. Margin: Entire.

*Spadix* (*reproductive organs*).—Size: Length: 3 cm to 4 cm. Diameter: 0.4 cm to 0.7 cm. Color: Base: RHS 9C. Upper part: RHS 9B. Position relative to spathe: Upright. Shape: Elongated. Apex: Rounded.

*Peduncle* (*flower stem*).—Length: 45 cm to 60 cm. Diameter: 0.8 cm to 1.2 cm. Color: Base: RHS 155A. Upper part: RHS 137A. Surface texture: Smooth. Strength: Strong.

Reproductive organs:

*Location of female organs.*—Basal position of the spadix.

*Location of male organs.*—Upper position of the spadix.

*Perianth* (*the floral envelope, calyx and corolla*).—Conspicuous.

*Pollen color.*—RHS 4C.

*Stamens.*—Not visible before pollen release.

*Pistil.*—Number: 10 to 20 per spadix. Color: RHS 9C.

Fruit (berries):

*Quantity of berries per plant.*—10 to 20.

*Color.*—RHS 144B.

*Size.*—Length: 4 cm to 5 cm (whole fruit). Width: 2.5 cm to 3.5 cm (whole fruit). Diameter: 0.6 cm to 0.8 cm (individual berry).

Disease and insect resistance:

*Disease resistance.*—No susceptibility to date.

*Pest resistance.*—No susceptibility to date.

COMPARISON WITH PARENTAL AND KNOWN CULTIVARS

When compared to the commercial variety 'Black Magic' (unpatented), 'Amarillo BLZ' has a less upright leaf attitude, darker green leaves, smaller throat spot and a darker yellow inner spathe colour.

When compared to the commercial variety 'Florex Gold' (unpatented), 'Amarillo BLZ' has longer flower stems and a larger, more rounded spathe shape.

When compared to the commercial variety 'Yellow Jacket BLZ' (U.S. Plant Pat. No. 20,217), 'Amarillo BLZ' has a taller plant height, less upright leaf attitude, longer petiole, broader leaf, presence of basal lobes and larger throat spot.

When compared to the commercial variety 'Solid Gold BLZ' (U.S. Plant Pat. No. 23,754), 'Amarillo BLZ' has a darker green upper petiole colour, green growing point colour and a taller plant height.

When compared to the female parent, 'Amarillo BLZ' has a greater density of leaf maculation, a lighter yellow inner spathe colour and longer flower stems.

I claim:

1. A new and distinct cultivar of calla lily plant as shown and described herein.

* * * * *